(12) United States Patent
Hoffmann et al.

(10) Patent No.: US 6,746,712 B2
(45) Date of Patent: Jun. 8, 2004

(54) DEVICE AND METHOD FOR REGULATING APPLICATION OF ADHESIVES AND/OR SEALANTS

(75) Inventors: Gunter Hoffmann, Bopfingen (DE); Volker Kels, Neuss (DE); Joerg Hurdelbrink, Reinsdorf (DE); Richard Scholta, Cologne (DE); Willi Borst, Florstadt (DE); Roland Heume, Gedern (DE)

(73) Assignee: Henkel Kommanditgesellschaft auf Aktien (Henkel KGaA), Dusseldorf (DE)

( * ) Notice: Subject to any disclaimer, the term of this patent is extended or adjusted under 35 U.S.C. 154(b) by 0 days.

(21) Appl. No.: 10/248,256

(22) Filed: Dec. 31, 2002

(65) Prior Publication Data

US 2003/0148018 A1 Aug. 7, 2003

Related U.S. Application Data

(63) Continuation of application No. PCT/EP01/13924, filed on Nov. 28, 2001.

(51) Int. Cl.$^7$ ................................................. B05D 5/10
(52) U.S. Cl. ..................... 427/208.6; 118/300; 118/313; 118/665; 118/688; 118/712; 427/207.1; 427/208.2; 427/208.4; 427/256
(58) Field of Search ................................ 118/300, 313, 118/665, 688, 712; 427/207.1, 208.2, 208.4, 208.6, 256

(56) References Cited

U.S. PATENT DOCUMENTS

| | | | |
|---|---|---|---|
| 3,887,110 A | 6/1975 | Porter | |
| 5,054,650 A | 10/1991 | Price | |
| 6,131,770 A | 10/2000 | Allen | |

FOREIGN PATENT DOCUMENTS

| | | |
|---|---|---|
| DE | 296 20 763 U | 2/1997 |
| DE | 201 00 107 U | 4/2001 |
| EP | 0 993 873 A2 | 4/2000 |

*Primary Examiner*—Bernard Pianalto
(74) *Attorney, Agent, or Firm*—Brooks Kushman P.C.

(57) ABSTRACT

The present invention pertains to an arrangement for the controlled application of adhesive to substrate. In at least one embodiment, the arrangement comprises a) an adhesive reservoir, b) a pump, c) an applicator head having at least one applicator nozzle, d) a volume throughput sensor, and e) a monitoring unit. The reservoir, the pump, and the applicator head are connected together by a conduit system carrying the adhesive. The volume throughput sensor and the monitoring unit are connected together by a pulse transmission line. The monitoring unit, the feed pump, and the applicator head are connected together by control lines. In at least one embodiment, the application of adhesive to substrates is controlled by measuring the volume throughput of the adhesive, transmitting signals indicative of volume throughout to the monitoring unit, and controlling the amount of adhesive applied to the substrate material in-line in response to the signals.

27 Claims, 3 Drawing Sheets

DEVICE AND METHOD FOR REGULATING APPLICATION OF ADHESIVES AND/OR SEALANTS

CROSS REFERENCE TO RELATED APPLICATIONS

This application is a continuation of PCT/EP01/13924 which was filed on Nov. 28, 2001, which claims priority from DE 100 60 030.1, filed Dec. 1, 2000, and DE 101 41 676.8, filed Aug. 25, 2001, which are hereby incorporated by reference.

BACKGROUND OF INVENTION

1. Field of the Invention

This invention relates to an arrangement for the controlled application of adhesives and/or sealants to substrate materials. The invention also relates to the use of this arrangement and to a process for controlling the application of adhesives and/or sealants to substrate materials.

2. Background Art

In many cases, continuous strips of adhesive and/or sealant, for example, have to be applied to a substrate material which is moved in endless form (for example in web form) or in the form of consecutive sections or blanks past an arrangement consisting in principle of an applicator head with an applicator nozzle. In other cases, the same substrate material has to be provided at several points with the same adhesive and/or sealant, continuous strips of adhesive and/or sealant, spots of adhesive and/or sealant, length-limited beads of adhesive and/or sealant or patches of adhesive and/or sealant having to be produced. For example, in the production of packages, webs or blanks of material have to provided with adhesive in the form of so-called glue spots, glue beads, or glue patches for fixing in the positions forming the packages.

In order to dose the adhesives and/or sealants, the applicator heads generally comprise valves which control the supply of the adhesives and/or sealants to the applicator nozzle via electronic control units.

For the majority of applications, it is often desirable to obtain a uniform application pattern and a particular quantity or dose of the adhesive and/or sealant to be applied and, in particular, to monitor the desired dose to be applied.

Application of the adhesive and/or sealant has to be monitored because, for example, blockages in the pipe system, the applicator head, the applicator nozzle, in any filters present or a leak at any point of the machine cannot always be reliably ruled out. Differences between the desired dose to be applied and the dose applied in practice can occur, for example, as a result of production-related variations in the feed pump pressure or through changes in viscosity produced, for example, by changes in temperature. The effect of such variations can be in particular that the quantity of adhesive and/or sealant applied is too small for the necessary bonding and/or sealing of the substrate material. Accordingly, efforts have often been made in the past to counteract such effects by including a so-called safety reserve of the adhesive and/or sealant to be applied in the theoretically necessary dose.

Safety reserves are included in particular in processes where the substrate materials have surfaces that are difficult to bond or seal, for example painted, printed or lined surfaces. The inclusion of a safety reserve is also necessary when the bond is subjected to severe tensile stress. This is the case, for example, when substrate materials are bonded together during a shaping or forming process and have a natural tendency to return to their original shape. This happens, for example, when substrate materials are bonded via edges, as for example in the edge banding of wood. Safety reserves are also included in processes where the sealant or adhesive is required to show high heat resistance, as for example where bonded or sealed substrate materials are filled with hot media. Heat resistance in this context generally means the ability of an adhesive layer permanently to withstand exposure to high temperatures without deformation.

Monitoring whether the required dose of adhesive and/or sealant is present on the substrate material is normally done by random sampling or continuously, for example by visual inspection and/or additionally by a) moisture measurements where the adhesive applied is water- or solvent-based, b) infrared sensors for determining the dose of adhesive and/or sealant applied to the substrate through the heat given off, c) gravimetrically by weighing correspondingly marked substrate materials before and after application of the adhesive and/or sealant, or d) microwave or ultrasound technology for measuring traces of adhesive and/or sealant or layers of adhesive and/or sealant.

The accuracy of the monitoring techniques listed above is not particularly high because of the methods used and additional external influencing factors (for example atmospheric humidity). This is another reason for the normal additional dose of the adhesive and/or sealant to be applied as a safety reserve.

If the adhesive and/or sealant is only applied inadequately, if at all, to the substrate material, rejection of the substrate material is generally the result. If it also taken into account that many processes where adhesives and/or sealants are applied to substrate materials now operate at high speeds, the economic loss attributable to rejects and the machine stoppages they involve caused by cleaning and repair work is considerable.

Accordingly, in order to be able to respond more quickly to interruptions in the application of the adhesives and/or sealants to substrate materials, there are advantages in processes where application of the adhesive and/or sealant is monitored between the storage container (reservoir) for the adhesive and/or sealant and the applicator nozzle and not just on the substrate material. Such processes are known.

EP 0 887 721 A1 discloses a monitoring system in which a monitor periodically collects input signals of a sensor and compares the collected signals with stored alarm limit values. The sensor picks up a characteristic of a liquid flowing through a distributor, for example the liquid nozzle pressure. A pressure sensor integrated in the applicator head measures the static pressure of the liquid with the nozzle closed and the dynamic pressure of the liquid with the nozzle open. When the nozzle is open, the pressure falls in dependence upon the throughflow volume. The measured pressures are compared with the predetermined reference pressures are thus monitored. This process allows conclusions to be drawn as to the correct pump pressure and the throughflow volume in the applicator head. However, the lower the throughflow of the liquid in the nozzle, the smaller the measured pressure difference between the dynamic pressure and the reference pressure. Accordingly, it is not possible to measure an adequate pressure difference where the throughflow of liquid is very small, for example less than 100 mg of liquid.

Utility Model No. 296 20 763.2 describes an adhesive applicator which consists of an adhesive reservoir, a feed pump and an applicator head comprising at least one applicator nozzle. The adhesive reservoir, the feed pump and the applicator head are connected by a pipe carrying the adhesive. At least one sensor for the adhesive volume flow rate between the feed pump and the at least one applicator nozzle is provided. The function of this sensor for the adhesive volume flow rate is to measure the volume of adhesive actually delivered by the feed pump to the at least one applicator nozzle. If in the course of a work cycle the sensor should detect that not enough adhesive, if any, is being delivered, a corresponding monitoring circuit triggers an immediate interruption in production readily discernible to the machine attendant.

The above-described systems monitor the application of adhesives and trigger an alarm in the event of interruptions in application, but are not used to regulate the dosage of adhesives. In addition, neither quantity determination nor density determination of the liquid can be carried out with these systems.

U.S. Pat. No. 5,646,737 discloses an arrangement for applying liquid, preferably photographic materials as coatings. Layer measurement of the applied liquid is possible with this arrangement. The quantity applied is calculated from the layer profile in the x and y directions. The use of an encoder enables the quantity applied to be controlled. However, measurement of the layer presupposes that the coated material is absolutely flat, that the thickness of the material remains absolutely constant and that coating is continuous. Accordingly, this application and measuring arrangement can only be used for surface coating on films or film-like materials.

SUMMARY OF INVENTION

In at least one embodiment, the present invention avoids the disadvantages of the prior art and improves and simplifies existing processes and machines for the application of adhesives and/or sealants. This includes, in particular, achieving improved monitoring of application, more accurate measurement of the quantity applied and control of the quantity of adhesives and/or sealants applied irrespective of the substrate material, the material surface (for example films, nonwovens, paperboard, wood, etc.) and the form of application (for example surface coating, spiral spray application, spot application, bead application). Accurate measurement of the quantity applied would be possible both with intermittent and with continuous forms of application.

In at least one embodiment, the present invention pertains to an arrangement for the controlled application of adhesives and/or sealants to substrate materials which comprises the following components: a) a reservoir for at least one adhesive and/or sealant, b) a feed pump, c) an applicator head with at least one applicator nozzle, d) a volume throughput sensor, and e) a monitoring unit with an associated data processing program.

The reservoir, the feed pump and the applicator head with at least one applicator nozzle are connected together by a conduit system carrying the adhesive and/or sealant. The volume throughput sensor and the monitoring unit with the associated data processing program are connected together by a pulse transmission line. The monitoring unit with the associated data processing program, the feed pump and the applicator head are connected together by control lines.

In at least one embodiment, the present invention also pertains to a process for the controlled application of adhesives and/or sealants to substrate materials wherein a) the volume throughput of the adhesive and/or sealant is measured by the volume throughput sensor, b) the electrical pulses picked up by the volume throughput sensor are passed to the monitoring unit with an associated data processing program, and c) the monitoring unit with the associated data processing program adapts the dose of adhesive and/or sealant applied to the substrate material in-line by continuous balancing the required and actual values and by actuating the feed pump and increasing or reducing its output accordingly.

BRIEF DESCRIPTION OF DRAWINGS

The arrangement according to the invention for the controlled application of adhesives and/or sealants to substrate materials is described in more detail in the following with reference to an embodiment illustrated in the accompanying drawings, wherein.

DETAILED DESCRIPTION

Figure 1:
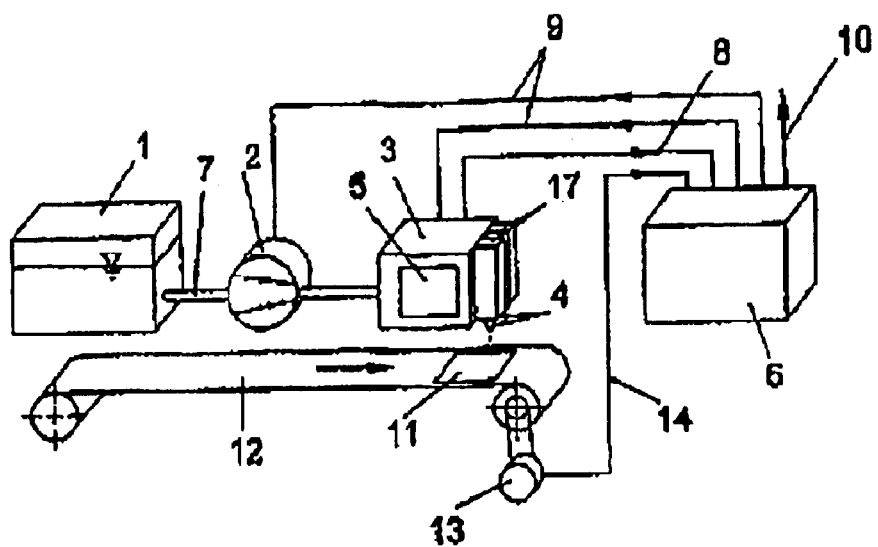
FIG. 1 is a perspective view of the arrangement according to the invention with a volume throughput sensor immediately preceding the applicator nozzles and with the monitoring unit as a measuring and control unit.

As required, detailed embodiments of the present invention are disclosed herein. However, it is to be understood that the disclosed embodiments are merely exemplary of the invention that may be embodied in various and alternative forms. The figures are not necessarily to scale, some features may be exaggerated or minimized to show details of particular components. Therefore, specific structural and functional details disclosed herein are not to be interpreted as limiting, but merely as a representative basis for the claims and/or as a representative basis for teaching one skilled in the art to employ the present invention. Also, unless specifically stated otherwise, adhesive means one or more adhesives, sealants, or a combination thereof.

At least one embodiment of the present invention pertains to an arrangement for the controlled application of adhesive to substrate materials (11) which essentially comprises the following components: a) a reservoir (1) for adhesive, b) a feed pump (2), c) an applicator head (3) with at least one applicator nozzle (4), d) a volume throughput sensor (5), and e) a monitoring unit (6) with an associated data processing program.

The reservoir (1), the feed pump (2) and the applicator head (3) with at least one applicator nozzle (4) are connected together by a pipe system (7) carrying the adhesive and/or sealant. The volume throughput sensor (5) and the monitoring unit (6) with the associated data processing program are connected together by a pulse transmission line (8). The monitoring unit (6) with the associated data processing program, the feed pump (2), and the applicator head (3) are connected together by control lines (9).

Starting from the reservoir (1), the adhesives and/or sealants are delivered by the feed pump (2) through a pipe system (7), which preferably comprises rigid and/or flexible pipes and may be cooled or heated, to an applicator head (3)

where they are applied by the at least one applicator nozzle (4) to a substrate material (11) disposed on a continuous or intermittent conveyor (12), for example in the form of a conveyor belt.

Intermittent feed pumps (2), for example piston pumps, or continuous feed pumps (2), for example gear pumps, may be used to generate pressure in the pipe system (7). The feed pump (2) may be operated both pneumatically and electronically.

The volume throughput of the adhesive and/or sealant is measured by the volume throughput sensor (5) which is preferably positioned between the feed pump (2) and the at least one applicator head (4). In one particular embodiment, the volume throughput sensor (5) is part of the applicator head (3) and is arranged immediately in front of (i.e., upstream) the at least one applicator nozzle (4) in the direction of flow of the adhesive and/or sealant. In this way, measurement delays and the effect of pressure variations on the measuring system can largely be ruled out.

On the principle of a star feeder, the quantity of adhesive and/or sealant flowing through the volume throughput sensor (5) is determined and transmitted in the form of electrical pulses to the monitoring unit (6). The volume throughput sensor (5) may be regarded as part of an automatic control circuit which monitors the actual volume throughput of the adhesive(s) and/or sealant(s) and signals changes, for example a shortage of adhesive and/or sealant. The volume throughput sensor (5) is preferably in the form of a gear pump operating in reverse because this type of volume throughput measurement is able to resolve particularly small mass transports down to a lower limit of 10 mg, based on a density of 1 g/ml, in differentiated form.

The volume throughput sensor (5) measures partial amounts of the adhesive and/or sealant as determined in advance by the gear tooth system. For every partial amount which is transported by the rotary movement of the interengaging teeth as produced by the volume throughput, an electrical pulse is released through the magnetoelectrical sensor. The magnetoelectrical sensor is generally a differential field plate sensor which lies above the ring of one of the two measuring gearwheels and which releases an electrical pulse for each tooth passing through beneath it. The mechanical part of such a sensor is known, for example, from DE 40 40 409 C1while particulars of the associated, actual sensor can be found in DE 40 42 397 C2.

In order to obtain greater accuracy of measurement, several differential field plate sensors may be used. In a preferred embodiment of the invention, the volume throughput sensor is equipped with two differential field plate sensors each with a separate preamplifier. The pulses on the corresponding channels 1 and 2 are offset through 90° and have to appear as symmetrical phases. The precise installation position—required for this purpose—of the differential field plate sensor on the volume throughflow sensor for the inductive measurement of the measuring star wheels is preferably achieved by a high-temperature-resistant plastic mounting, for example of Teflon.

The volume throughput sensor (5) is suitable for use at temperatures in the range from 20° C. to 300° C., preferably at temperatures in the range from 80° C. to 250° and more particularly at temperatures in the range from 160° to 210° C.

Depending on the distance between the measuring gearwheels, the resolution is between 0.001 ml and 2 ml, preferably between 0.003 ml and 1.5 ml and more particularly between 0.005 ml and 1 ml. The choice of the volume throughput sensor (5) to be used depends upon the viscosity and dose of the adhesive and/or sealant to be applied.

The electrical pulses released by the magnetoelectrical sensor are passed to the monitoring unit (6) with the associated data processing program via a corresponding pulse transmission line (8).

The monitoring unit (6) with the associated data processing program is understood in the following to be a measuring and monitoring unit which monitors the dose of adhesive and/or sealant applied to the substrate material (11) in-line via by continuous balancing of the required and actual values and adapts it where necessary to the required value.

The data processing program of the monitoring unit (6) is based on standard software to IEC Standard 1131-3 which relates to language elements and programming rules for the worldwide programming languages for memory-programmable control systems. More specifically, the STEP 7 programming software from the Siemens SIMATIC product range conforms to that Standard. The software is adapted to the requirements of the arrangement according to the invention and processes the data required for the continuous "required value/actual value" balancing, freely selectable upper and lower limits being selected as limit values for the dose of adhesive and/or sealant applied within which adaptation to the required value should take place. If, for example, the required dose of adhesive and/or sealant slowly decreases through an incipient blockage of the pipe system (7), the feed pump is actuated and application of the adhesive and/or sealant is controlled by the release of an analog signal and adapted to the required value.

If the feed pump (2) is a pneumatically operated feed pump, a corresponding commercially available electropneumatic controller is required. The electromagnetic controller is preferably connected directly to the compressed air input of the pneumatic feed pump. If the feed pump (2) is an electronically operated feed pump, a corresponding controller card is required to control the pump frequency.

In a particularly preferred embodiment, the arrangement according to the invention contains an encoder (13). The function of encoders (13) or even angle-of-rotation sensors is to determine the angle of rotation or the length and direction of a rotary or linear movement of moved bodies. To this end, the moved bodies have a magnetically, optically or otherwise coded zone and are moved past a fixed sensor element. An absolute value in respect of the angular position and direction value (for example rotational speed) is determinable in each position of the coded zone relative to the sensor.

The key components of optical encoders, for example, are the emitter system, a scanning plate, normally a scanning disk or a scanning signal, and the detector system. The emitter system normally consists of a light-emitting diode or laser diode. The light beam produced by the laser diode is modulated by the scanning plate. The scanning plate is connected to the moved body and has a periodic opening pattern. The detector system picks up the transmitter signal of the laser diode modulated by the scanning plate and provides the information on the counting pulse and direction of movement at its output.

In principle, while any commercially available encoders may be used, encoders with an operating voltage of 10 to 30 volts are preferred. Other characteristic data of the encoder, for example pulse count, rotational speed, transmission ratio, etc., are included in the programming of the monitoring unit (6) with the associated data processing program.

By means of the encoder (13), it is possible to determine the distance traveled by substrate materials (11) past the at least one applicator nozzle (4) and the time taken to travel that distance. The encoder (13) and the monitoring unit (6) with the associated data processing program are connected to one another by a corresponding transmission line (14).

The information provided by the encoder (13) is received by the monitoring unit (6) with the associated data processing program and electronically processed to enable the quantity and length of adhesive and/or sealant applied to be controlled as a function of speed. This speed-dependent control is based on the speed at which the substrate material (11) is transported past the applicator nozzle (4). Since the information provided by the encoder (13) is continuously picked up and processed by the monitoring unit (6) with the associated data processing program, the quantity of adhesive and/or sealant applied and the application time can also be permanently monitored and not just controlled as a function of speed.

As already mentioned elsewhere, the volume throughput sensor (5) releases an electromagnetic pulse on delivery of a certain volume, for example one pulse for a volume 10 ml. The choice of the measuring cell is preferably governed by the viscosity of the liquid, a measuring cell with a relatively large volume per pulse being selected with increasing viscosity. The larger the measuring cell, however, the greater the accuracy of measurement. In order to improve accuracy of measurement, particularly where application is intermittent and particularly small quantities have to be measured, the use of an encoder is particularly preferred. Compared with the resolution of the pulses released by the volume throughput sensor (5), the resolution of the pulses released by the encoder (13) is appreciably higher. Based on a certain application length, only one pulse is generated by the volume throughput sensor (5) whereas the encoder (13) produces a much greater number of pulses. The unknown quantity of adhesive applied between two pulses of the volume throughput sensor (5) for a certain dose is calculated by adding a conversion factor to the volume throughput sensor pulse per encoder pulse by means of the monitoring unit (6) with the associated data processing program.

The monitoring unit (6) with the associated data processing program is designed in such a way that, before the measuring cycle, measurement is calibrated to weight determination so that the quantity of adhesive actually applied is determined.

The arrangement according to the invention is used in processes for the controlled application of adhesives and/or sealants to substrate materials (11) where a) the volume throughput of the adhesive and/or sealant is measured by a volume throughput sensor (5), b) the electrical pulses picked up by the volume throughput sensor (5) are passed to a monitoring unit (6) with an associated data processing program, and c) the monitoring unit (6) with the associated data processing program adapts the dose of adhesive and/or sealant applied to the substrate material (11) inline via continuous balancing of the required and actual values to the required value by actuating the feed pump (2) and increasing or reducing its output accordingly.

Exceeding of the selected limit values or failure to reach them is recorded by the monitoring unit (6) with the associated data processing program as a so-called fault, processed and preferably signaled as a fault by electronic and/or acoustic functions. To this end, the monitoring unit (6) with the associated data processing program preferably has an output (10) for the external processing of fault signals. For example, a computer monitor may be connected up via that output so that any fault is displayed on the screen. In addition or alternatively, acoustic functions (for example a siren) or optical functions (for example a warning lamp) may be connected via the output (10). However, the control unit (6) with the associated data processing program may even completely interrupt the supply of adhesive and/or sealant if, for example, adaptation to the required value is no longer possible and in order, for example, to carry out the cleaning measures necessitated by the fault.

The process is particularly suitable for applying glues, pastes, dispersion-based adhesives, solvent-based adhesives, contact adhesives, two-component adhesives, pressure-sensitive adhesives, pressure-sensitive hotmelt adhesives and hotmelt adhesives. Two-component adhesives, pressure-sensitive adhesives, pressure-sensitive hotmelt adhesives and hotmelt adhesives have proved to be particularly suitable.

Hotmelt adhesives are generally water-and solvent-free adhesives which are applied to the parts to be bonded from the melt and which set physically by hardening on cooling after the parts to be joined have been fitted together. Hotmelt adhesives are widely used in industry, for example for bonding and lamination in the furniture, shoe, electrical, packaging and paper industries. In the packaging and paper industries, they are used, for example, for sealing or closing boxes, and for laminating multilayer papers or for binding books.

For the production of medical articles (for example plasters, bandaging material) or hygiene articles (for example diapers, sanitary napkins), various substrate materials are joined together using hotmelt adhesives. Thus, such materials as polyolefin films, for example polyethylene films or polypropylene films, polyolefin nonwovens, for example polyethylene nonwovens or polypropylene nonwovens, polyurethane films, polyurethane foams, films or moldings of cellulose derivatives, for example of cellulose (tissues), films or moldings of polyacrylates or polymethacrylates, films or moldings of polyesters, can be joined together. The same materials and different materials may be joined.

Hotmelt adhesives are widely used as labeling adhesives in the food and beverage industry. In the cigarette industry, hotmelt adhesives are used, for example, for bonding filter tips.

Various polymers/copolymers are available as base materials for hotmelt adhesives including, for example, —polycondensates, such as polyamide resins, copolyamides, polyamide/EVA copolymers, polyamide/siloxane copolymers, polyetheramides, polyesteramide imides, polyetherester amides, polyester amides and copolyesters, saturated polyesters, —polyadducts, such as reactive and nonreactive, linear or lightly branched thermoplastic polyurethanes and—polymers, such as ethylene copolymers, copolymers of ethylene with unsaturated carboxylic acids, ethylene/vinyl acetate copolymers, ethylene terpolymers, for example ethylene acrylate terpolymers, propylene/hexene, SIS and SBS copolymers and other thermoplastic elastomers and amorphous polyolefins, for example polyethylene, polyolefins produced via Metallocen catalysis, more particularly PP, and finally polybutene.

Preferred polymers are homo- and/or copolymers of olefinic monomers, more particularly α-olefins. These homo- and/or copolymers are obtained by polymerization of olefinic monomers with a chain length of $C_2$ to $C_{20}$. Homo- and/or copolymers of olefinic monomers produced using metallacene catalysts are particularly preferred, as are homo- and/or copolymers of olefinic monomers with no functional groups.

The polymers mentioned largely determine the actual properties of the adhesive layer in regard to adhesion, strength and temperature behavior. Other special properties (for example cohesion, viscosity, etc.) can be obtained by additions of, for example, tackifying resins, waxes, plasticizers, for example oils, stabilizers, antioxidants and/or fillers.

Actual products for bonding and/or sealing are obtainable, for example, from Henkel KGaA, Dorus or Teroson. Adhesives for flexible packages or for the refining of paper are available under the names of Liofol, Lio-Clean or Liotron. Adhesives used for the production of, for example, coatings, self-adhesive labels or adhesive tapes are available under the names of Euromelt, Dorus-DP, Adhesin J, Sichello J or Liotron. Adhesives used, for example, for labeling plastics include such names as Euromelt, Pekal, Optal or Smeltan. Lioseal or Liotext, for example, are used for heat sealable coatings or text laminations. Such products as, for example, Technomelt, Adhesin and Curo are used for box packaging (external box closures, folding box closures, box erection), low-temperature packaging or palette stabilization. Sanicare adhesives, for example, are used in the hygiene sector (for example baby diapers, feminine hygiene or incontinence) or medical field (for example OP cloths, bandages, plasters). Tobacoll adhesives, for example, are used in cigarette manufacture (side seam closure, packaging, filter production, etc.). Adhesives used, for example, in the bonding of insulating glass, cable filling compounds, wood processing or shoe manufacture include, for example, Terostat, Macromelt and Macroplast.

The process is suitable for adhesives and/or sealants which have a viscosity at the corresponding processing temperatures of 20 mPas to 100,000 mPas, preferably in the range from 20 mPas to 40,000 mPas and more particularly in the range from 20 mPas to 20,000 mPas, as measured according to ASTM D 3236. By corresponding processing temperatures are meant temperatures in the range from 20 to 300° C., preferably in the range from 40 to 250° C. and more particularly in the range from 40 to 200° C. These adhesives and/or sealants preferably show no signs of stringing on leaving the applicator nozzle (3), particularly if small quantities of the order of 10 to 100 mg are being applied. Adhesives and/or sealants with a viscosity of 20 mPas to 20,000 mpas, as measured according to ASTM D 3236, are particularly suitable for applying such small quantities, optionally in combination with an applicator head (3) having at least one applicator nozzle (4), the at least one applicator nozzle (4) being in the form of a spiral spray nozzle. Ideally, the adhesives and/or sealants to be applied in particularly small doses do not contain any solids. If solids are present, their particle size should be no greater than 5 micrometers.

The process is particularly suitable for adhesives and/or sealants which have a constant viscosity at the corresponding processing temperature with a variation of ±50% over the usual processing time. By the usual processing time are meant times of 15 minutes to 72 hours.

Hotmelt adhesives, for example, are known to undergo material changes under the effect of temperature, depending on their composition. Depending on the degree and duration of the temperature effect, such changes can result in the evaporation of more volatile constituents and/or in at least partial thermal degradation. This thermal degradation can produce volatile decomposition products and/or so-called cracking or carbonization products, the crosslinking of unsaturated compounds already present or formed by the effect of temperature generally occurring as a preliminary step to the cracking or carbonization process. These material changes produced by the effect of temperature are reflected, for example, in a change in viscosity and also in an incipient or established inhomogeneity of a previously homogeneous composition, in partial or complete insolubility in generally organic solvents in which the composition was completely soluble before the effect of temperature and/or in the form of a change in the color and aggregate state of, for example, pale yellowish liquids to black paint-like products.

The arrangement according to the invention is particularly suitable for the controlled application and dosing of adhesives and/or sealants on a production scale. Quantities of up to 300 l/min. can be applied under control in dependence upon the viscosity of the adhesive and/or sealant. The maximum speed at which the substrate material (11) can be transported past the applicator nozzle (4) with application still under control corresponds to the speed of the high-performance machines used in the production process.

The process according to the invention for the controlled application of adhesives and/or sealants to substrate materials (11) can be carried out both intermittently and continuously. To this end, the volume throughput sensor (5) is integrated as required in commercially available applicator heads used for producing spots, beads or for surface coating with adhesives and/or sealants:—For example, the spot application of adhesives and/or sealants can be monitored and controlled from a quantity of 10 mg, based on a density of 1 g/ml, up to 2,000 spots per minute.—On the basis of the information supplied by the encoder (13) to the monitoring unit (6) with the associated data processing program and its continuous collection and processing, the application of adhesives and/or sealants in bead form is monitored and controlled in both length and dose, in surface coating, for example with nozzle contact or by spraying, is monitored and controlled in regard to quantity, based on the application area, and kept constant or adapted to the speed in the event of variations in the speed of travel of the substrate material (11).

The arrangement according to the invention may be used to determine the density and measure the quantity of adhesives and/or sealants applied. The accuracy of measurement increases with increasing doses.

In a preferred embodiment, the arrangement according to the invention is used to determine the density of adhesives and/or sealants which have a viscosity at the corresponding processing temperatures of 20 mPas to 100,000 mPas, as measured according to ASTM D 3236. To this end, a freely selectable quantity of the adhesive and/or sealant is collected at the applicator head (3) and the weight of the collected adhesive and/or sealant is determined.

The volume throughput sensor (5) which is connected to the monitoring unit (6) with the associated data processing program via a pulse transmission line (8) generates a number of pulses associated with the quantity of adhesive and/or sealant removed. Since a particular volume of adhesive and/or sealant is delivered per pulse, the density can be calculated with the aid of the data processing program belonging to the monitoring unit (6) and displayed, for example on a computer monitor. Production-related tolerances of the measuring gearwheels and resulting deviations from the theoretical partial volume are taken into account and are included as tolerance factors in the evaluation.

In another preferred embodiment, the arrangement according to the invention is used to determine the applied dose of adhesives and/or sealants which have a viscosity at the corresponding processing temperature of 20 mPas to 100,000 mPas, as measured according to ASTM D 3236. If the density of the adhesive and/or sealant to be applied is known or has been determined, for example, by the method described above, the weight of the adhesive and/or sealant delivered can be calculated with the aid of a data processing program belonging to the monitoring unit (6) in conjunction with the pulse count supplied by the volume throughput sensor (5) to the monitoring unit (6) along the pulse transmission line (8) and displayed, for example on a computer monitor. Production-related tolerances of the measuring gearwheels and resulting deviations from the theoretical partial volume are taken into account and are included as tolerance factor in the evaluation.

Ideally, the density of the adhesive and/or sealant remains constant after the calibration thus effected.

In particular, very small quantities of the adhesive and/or sealant applied or to be applied can thus be measured and dosed. As mentioned elsewhere, very small quantities are understood to be quantities of 10 mg to 100 mg, based on a density of 1 g/ml.

The process according to the invention has the advantage over known processes, particularly in the surface coating of substrate materials (11) with adhesives and/or sealants, for example in the coating of nonwovens with adhesives, that the weight of the adhesive and/or sealant applied is directly determined by an in-line process and does not have to be determined, for example, off-line by random determination of the weight per unit area of substrate materials (11).

For additionally checking whether the adhesive and/or sealant, besides having been applied in the exact dose, has also been uniformly distributed on the substrate material, a corresponding and known measuring unit with infrared sensors is optionally used in the process.

The process according to the invention for applying adhesives and/or sealants has an absolute measuring accuracy of ±0.5% of the quantity applied in relation to conventional processes. Conventional processes are understood in particular to be processes where the adhesive and/or sealant is applied to carrier materials (11) which are present in the form of blanks of various materials. The quantity applied is monitored, for example, by determining the weight of up to 100 substrate materials (11) before and after application of the adhesive and/or sealant, statistically evaluating the results and calibrating the applicator in accordance with the evaluation. The weight of adhesive and/or sealant applied is often light in relation to the weight of the substrate material (11) which results in greater accuracy of the weight determination. Other factors, for example the release of moisture from the substrate material or the adhesive and/or sealant after application to the substrate material (11) and before the weight determination, increase the scatter range of the measurement.

The accuracy with which the adhesives and/or sealants are constantly applied and dosed for the first time on a production scale and with which the quantity applied can be determined enables the arrangement according to the invention to be used not only as a permanent fixture in existing processes for applying adhesives and/or sealants, but also as a device installed temporarily in existing installations, for example as a measuring and control unit for monitoring new adhesives and/or sealants.

It should be emphasized that all conventional measuring processes which measure the actual application to the substrate material in the course of production can only be used to a limited extent for determining the quantity applied. Surface coating can certainly still be reproducibly measured. In the case of spot and bead application, safe measurement of length and position is possible. However, quantities applied cannot be measured with milligram accuracy. In cases where, for example, low-viscosity liquids are applied by spraying, for example to a nonwoven of the same color, safe measurement is no longer possible. In addition, measuring systems for the actual application always have to be designed according to the particular use and provide faulty results as a result of disturbing outside influences such as, for example, changes in the ambient temperature, color changes, moisture, etc. The measuring process according to the invention can be universally used and does not react to the disturbing influences mentioned above. Measurement of the throughput volume guarantees application with milligram accuracy. This is a pre-requisite for accurate quantity control.

The arrangement according to the invention and its use in processes for applying adhesives and/or sealants contributes greatly towards improving quality. Because the quantity of adhesive and/or sealant delivered is continuously measured and controlled, less waste is produced. The usual 10 to 30% by weight reserve added to the theoretically necessary dose of adhesive and/or sealant is no longer necessary or at least can be drastically reduced. Accordingly, the disadvantages associated with the overdosing of adhesives and/or sealants, such as for example the adhesion of the coated substrate materials (11) to the conveyors (12) or the soiling of equipment by adhesive and/or sealant residues, are also eliminated.

The process according to the invention using the arrangement according to the invention is particularly suitable for applying adhesives, preferably hotmelt adhesives, to substrate materials (11) for medical articles and hygiene articles.

The arrangement according to the invention and its use in processes for the application and application measurement of adhesives and/or sealants may also be used for the application and application measurement of low-viscosity and high-viscosity liquids of all kinds, more particularly liquids which have a viscosity at corresponding process temperatures of 20 mPas to 100,000 mPas, as measured according to ASTM D 3236.

Liquids which comply with that standard are widely used, for example, in the food industry, the cosmetics industry and the chemical industry and, for example, are pastes or paints.

The arrangement shown in FIG. 1 for the controlled application of adhesives and/or sealants to substrate materials comprises a) a reservoir for an adhesive and/or sealant (1), b) a feed pump (2), c) an applicator head (3) with at least one applicator nozzle (4), d) a volume throughput sensor (5), and e) a monitoring unit (6) with an associated data processing program.

The reservoir (1), the feed pump (2) and the applicator head (3) with at least one applicator nozzle (4) are connected together by a pipe system (7) carrying the adhesive and/or sealant. The volume throughput sensor (5) and the control unit (6) with the associated data processing program are connected together by a pulse transmission line (8). The monitoring unit (6) with the associated data processing program, the feed pump (2) and the applicator head (3) are connected together by control lines (9). The monitoring unit (6) with the associated data processing program has an output (10) for the external processing of fault reports.

The volume throughput sensor (5) is positioned between the feed pump (2) and the—in this example two—applicator nozzles (4). As already mentioned, the function of the volume throughput sensor (5) is to monitor the volume throughput of the adhesive and/or sealant delivered by the feed pump (2) from the reservoir (1) to the applicator nozzles (4). The volume throughput sensor (5) is part of the applicator head (3) and is located immediately in front of the two applicator nozzles (4) facing in the direction of flow of the adhesive and/or sealant. This arrangement minimizes any pressure variations occurring between the applicator nozzles (4) and the volume throughput sensor (5) and thus improves the accuracy of measurement. The volume throughput of adhesive and/or sealant through the volume throughput sensor (5) is measured in the form of electrical pulses and passed to the monitoring unit (6).

The monitoring unit (6) processes the electrical pulses with a corresponding associated data processing program and, by continuous balancing of the required and actual values, adapts the quantity of adhesive and/or sealant applied to the substrate material (11) in-line to the required value by actuating the feed pump (2) so that its output is increased or reduced accordingly.

In the preferred embodiment illustrated, the monitoring unit (6) is connected to an encoder (13) by a corresponding transmission line (14). By means of the encoder (13), it is possible to determine the distance traveled by substrate materials (11) past the applicator nozzles (4) and the time taken to travel that distance. The information provided by the encoder (13) is received by the monitoring unit (6) with the associated data processing program and electronically processed and enables the quantity and length of adhesive and/or sealant applied to be controlled as a function of speed.

In the interests of clarity, FIG. 1 also shows a continuous or intermittent conveyor (12), for example in the form of a conveyor belt, and a substrate material (11), for example a box blank to be glued, arranged thereon.

Figure 3:
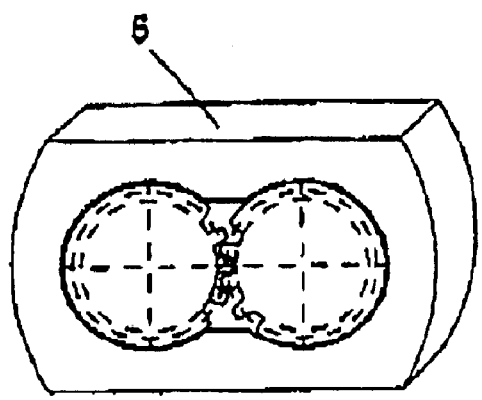
FIG. 3 is a perspective view of a known volume throughput sensor.

In the interests of completeness, FIG. 3 shows a commercially available volume throughput sensor (5) which needs no explanation.

In an actual and preferred embodiment of the arrangement, the applicator head (3) is in the form of a square housing (3') and is provided with an opening (15) which corresponds in shape to the housing of the volume throughput sensor (5) and in which the volume throughput sensor (5) is placed. On its downstream side, the volume throughput sensor (5) communicates through a channel (16) in the housing (3') with the valve housing (17) of the at least one applicator nozzle (4) fitted externally to the housing (3').

Figure 2:
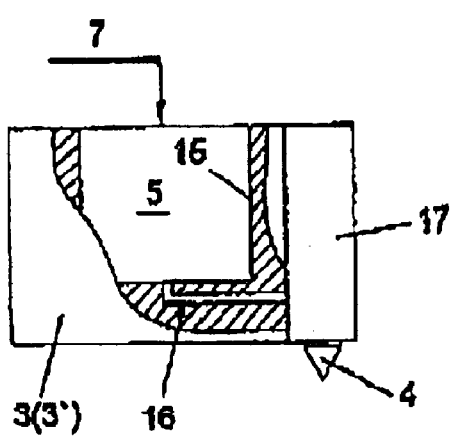
FIG. 2 is a section through an embodiment of the housing accommodating the volume throughput sensor.

The valve housing (17) shown in FIG. 2 does not require any explanation either because there is nothing different in such valve housings (17) with their applicator nozzles (4).

Description of the Measurement Principle

In the interests of a better understanding, the measurement principle is explained in the following with reference to three examples:
1. intermittent glue bead application
2. continuous surface application
3. dosing 1. Intermittent Glue Bead Application Measurement was based on the following data:
application length 34 mm
volume throughput sensor with a resolution of 1 pulse=10 mg (density=1 g/ml)
encoder with 1,000 pulses/revolution
transmission encoder conveyor belt: 1 revolution of the encoder=69 mm traveled by the conveyor.

Figure 4:
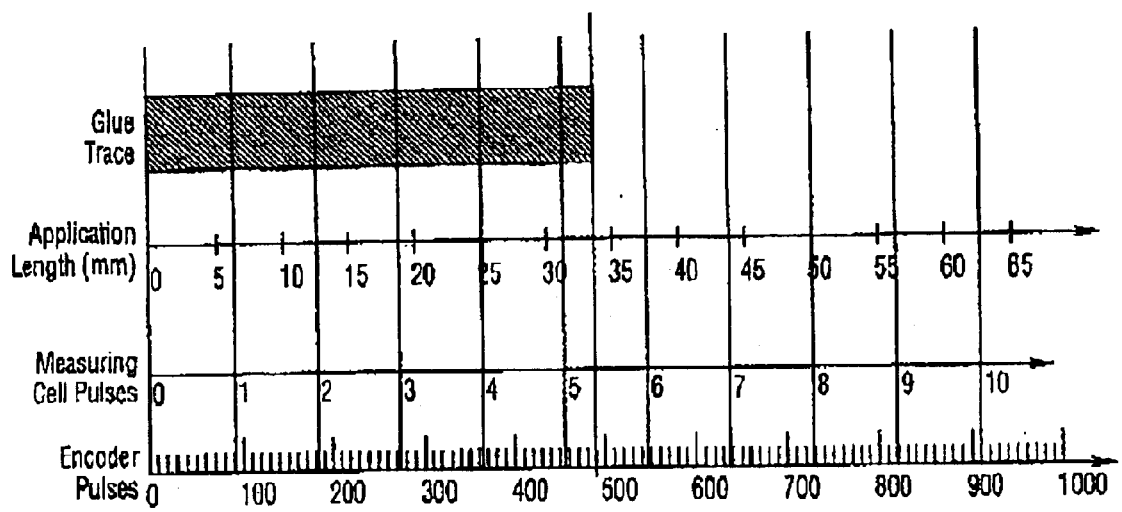
FIG. 4 is a graph illustrating the measurement principle with reference to intermittent glue bead application.

Making reference to FIG. 4, FIG. 4 illustrates the measurement principle (calculation) with reference to intermittent glue bead application. As further explained herein, the glue trace length is calculated by trigger length and belt speed. From the relation between sensor pulse and encoder pulse, the precise amount of applied adhesive can be calculated as being 53.846 mg in a glue trace length of 34 mm (the relation between encoder pulse and sensor pulse is explained above).

The following data are measured:
opening time of the glue module (valve housing)= measurement trigger length=0.2 s
volume throughput sensor pulses=5
encoder pulses=490
ratio of volume throughput sensor pulses to encoder pulses=constant
belt speed=10.2 m/min.

The glue trace length of 34 mm is obtained from the trigger length and the belt speed.

The quantity applied lies between the 5th and 6th pulses of the volume throughput sensor. The measured number of 5 pulses amounts to 50 mg for 455 pulses of the encoder. If the 5 pulses of the volume throughput sensor are divided by the 455 pulses of the encoder, a pulse rating of 0.010989=1/91 is obtained.

The residual quantity after the 5th pulse is calculated from 490−455=35 encoder pulses 35 encoder pulses×1/91 pulse rating=0.3846 volume throughput sensor pulses×10 mg/p=3.846 mg.

The quantity applied comes to 50+3.846=53.846 mg.

2. Continuous Surface Application

Figure 5:
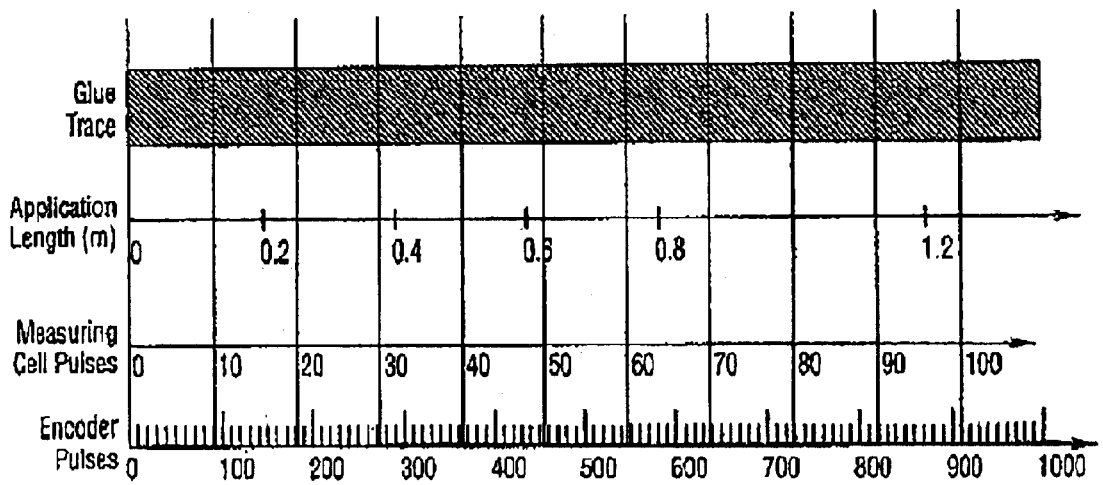
FIG. 5 is a graph illustrating the measurement principle and precision with reference to continuous surface application.

Measurement was based on the following data:
application width 50 mm
volume throughput sensor with a resolution of 1 pulse=10 mg (density 1 g/ml)
encoder with 1,000 pulses/revolution
transmission encoder-film web: 1 revolution of the encoder=1.375 m film web Making reference to FIG. 5, FIG. 5 illustrates the measurement principle (calculation) and precision with reference to continuous surface application. If the application width is known (here: 50 mm) it can be calculated starting from a certain number of sensor pulses (here e.g., 50), the number of respective encoder pulses (here: 456), and the speed of the belt (which is entered in the computer program at the beginning of the trial) the length of applied glue (here: 0627 in). As explained below the application weight is 15.9489 g/m$^2$.

The following data are measured:
measuring cycle every 50 incoming pulses of the volume throughput sensor
encoder pulses per measuring cycle=455

With the 50th pulse of the volume throughput sensor, 455 pulses are measured by the encoder.

455 encoder pulses=0.625625 m film web.

With the application width of 50 mm, the application area measures 0.05 m×0.625625 m=0.0312812 m$^2$ and, with 50 volume throughput sensor pulses=500 mg=0.5 g, the weight applied per unit area comes to 0.5 g/0.0312812 m$^2$=15.984 g/m$^2$. Since the measuring cycle is started by the pulses of the volume throughput sensor, the application length decreases with increasing coating weight, i.e., the next measurable higher coating weight comes with the 50th volume throughput sensor pulse and 454 encoder pulses.

454 encoder pulses=0.62425 m film web×0.05 m=0.0312125 m$^2$.

Coating weight per unit area=0.5 g/0.0312125 m$^2$=16.0192 g/m$^2$.

The next measurable lower coating weight comes with the 50th volume throughput sensor pulse and 456 encoder pulses=0.627 m film web×0.05 m=0.03135 m².

Coating weight per unit area=0.5 g/0.031 35 m²=15.9489 g/m².

Since the resolution of the encoder is the basis for the quantity determination in this measuring process, a measuring accuracy of ±0.11% is obtained in this process because 455=100% and 1 pulse=0.22%.

3. Dosing

The measuring system may be used as a dosing unit. The dose lies within the grid of the volume throughput sensor, i.e., for example (density=1 g/ml) 10 mg+10 mg + . . . +10 mg+ . . . In this version, an encoder is unnecessary. The monitoring unit controls the valve housing and hence the opening time via a control line. The dose is determined in advance by setting the pulse count of the volume throughput sensor as the required value at the monitoring unit. In addition, a max. dosing time is fed in. In the dosing process, reaching of the required dose and the dosing time taken to reach it are monitored. The dose is always reached as long as filling (adhesive) is present under pressure in the application system. Changes in the throughflow rate through changes in pressure or blockages in filters or nozzles of the valve housing are determined by varying the dosing time. The feed pump (pressure) is controlled by the monitoring unit so that the dose flows within the predetermined dosing time. If the dose is not reached in the max. predetermined dosing time, a fault report is issued.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. An apparatus for the controlled application of adhesive to substrates, the apparatus comprising the following components:
    a) a reservoir for containing a supply of adhesive,
    b) a feed pump,
    c) an applicator head having at least one applicator nozzle,
    d) a volume throughput sensor, and
    e) a monitoring unit with an associated data processing program, the reservoir, the feed pump and the applicator head being fluidly connected by a conduit system capable of transporting adhesive, the monitoring unit being operable to receive signals from the volume throughput sensor, and the monitoring unit being operable to control the feed pump and the applicator head in response to the signals received from the volume throughput sensor.

2. The apparatus of claim 1, wherein the volume throughput sensor is positioned between the feed pump and the at least one applicator nozzle.

3. The apparatus of claim 1, wherein the volume throughput sensor comprises a gear pump operating in reverse.

4. The apparatus of claim 1, wherein the volume throughput sensor is part of the applicator head and is positioned in front of the at least one applicator nozzle facing in the direction of flow of the adhesive.

5. The apparatus of claim 1, wherein the applicator head comprises a square housing and is provided with an opening which corresponds in shape to the housing of the volume throughput sensor and in which the volume throughput sensor is placed, the volume throughput sensor on its downstream side communicating through a channel in the housing with the valve housing of the at least one applicator nozzle fitted externally to the housing.

6. The apparatus of claim 1, wherein the volume throughput sensor is integrated in the applicator head.

7. The apparatus in claim 1, wherein the monitoring unit is operable to receive transmissions from an encoder.

8. The apparatus of claim 1, wherein the monitoring unit has an output for externally processing fault reports.

9. The apparatus of claim 1, wherein the apparatus is installed in processing equipment for applying adhesives.

10. The apparatus of claim 1, wherein the signals are pulse signals.

11. A process for the controlled application of adhesive to substrates using the apparatus of claim 1 wherein
    a) the volume throughput of the adhesive is measured by the volume throughput sensor,
    b) the electrical pulses picked up by the volume throughput sensor are transmitted to the monitoring unit, and
    c) the monitoring unit controls the amount of adhesive applied to the substrate material in-line by continuous balancing of the required and actual values to the required value by actuating the feed pump and increasing or reducing the output of the feed pump.

12. The process of claim 11, wherein the monitoring unit with the associated data processing program interrupts the delivery of adhesive when adjusting the amount of adhesive to the required value is not possible.

13. The process of claim 12, wherein exceeding a selected limit value or failing to reach a selected limit value generates a signal indicative of a fault.

14. The process of claim 11, wherein information provided by an encoder is transmitted to the monitoring unit and electronically processed to control the quantity and length of adhesive applied as a function of speed.

15. The process of claim 11, wherein the adhesive is selected from the group consisting of glues, pastes, dispersion-based adhesives, solvent-based adhesives, contact adhesives, two-component adhesives, pressure-sensitive adhesives, pressure-sensitive hotmelt adhesives and hotmelt adhesives.

16. The process of claim 15, wherein the adhesive is a hotmelt adhesive containing homo- and/or copolymers of olefinic monomers.

17. The process of claim 16, wherein the homopolymer and/or copolymers are produced from olefinic monomers using metallocene catalysts.

18. The process of claim 11, wherein the adhesive has a viscosity at temperatures from 20° C. to 300° C. of 20 mPas to 100,000 mPas, as measured according to ASTM D 3236.

19. The process of claim 11, wherein the adhesive to be applied has a constant viscosity with a variation of ±50% for up to 72 hours at temperatures of up to 300° C.

20. The process of claim 11, wherein the controlled application of adhesive to the substrates is carried out intermittently or continuously.

21. The process of claim 11, wherein the adhesive has a viscosity at temperatures from 20° C. to 300° C. of 20 mPas to 100,000 mPas as measured according to ASTM D 3236.

22. The process of claim 11, wherein the controlled application of the adhesive is performed on a production scale.

23. The process of claim 11, wherein the controlled application of the adhesive is performed in quantities of 10 mg to 100 mg of adhesives based on a density of 1 g/ml.

24. The process of claim 11, wherein the substrates are selected from the group consisting of medical articles and hygiene articles.

25. An apparatus for the controlled application of an adhesive to substrates, the arrangement comprising:
- a) a reservoir for containing adhesive,
- b) a feed pump,
- c) an applicator head having at least one applicator nozzle,
- d) a volume throughput sensor located between the feed pump and the applicator nozzle, and
- e) a monitoring unit having an associated data processing program,
- f) a conduit system fluidly connecting the reservoir, the feed pump and the applicator head with at least one applicator nozzle, the monitoring unit being operable to receive pulse transmissions from the volume throughput sensor, and the monitoring unit being operable to control the feed pump and the applicator head in response to transmissions from the volume throughput sensor.

26. The apparatus of claim 25, further comprising (g) an encoder capable of communicating with the monitoring unit.

27. A process for the controlled application of adhesive to substrates, said process comprising:
- a) providing an arrangement comprising:
  - i) reservoir for containing a supply of adhesive,
  - ii) a feed pump,
  - iii) an applicator head having at least one applicator nozzle,
  - iv) a volume throughput sensor located between the feed pump and the applicator nozzle, and
  - v) a monitoring unit with an associated data processing program, the reservoir, the feed pump and the applicator head being fluidly connected by a conduit system capable of transporting the adhesive, the monitoring unit being operable to receive volume signals from the sensor, and the monitoring unit being operable to control the feed pump and the applicator head,
- b) employing the volume throughput sensor to measure the volume throughput of the adhesive,
- c) detecting electrical pulse signals indicative of the volume of adhesive to be applied by the volume throughput sensor and transmitting the detected pulse signals to the monitoring unit, and
- d) controlling the amount of adhesive applied to the substrate in-line by continuous monitoring the volume of adhesive to be applied and selectively adjusting the output of the feed pump in response to the signals.

* * * * *

UNITED STATES PATENT AND TRADEMARK OFFICE
CERTIFICATE OF CORRECTION

PATENT NO. : 6,746,712 B2  
APPLICATION NO. : 10/248256  
DATED : June 8, 2004  
INVENTOR(S) : Hoffmann et al.

Page 1 of 1

It is certified that error appears in the above-identified patent and that said Letters Patent is hereby corrected as shown below:

Title Page, please insert:

--(30)  Foreign Application Priority Data  
      Dec 1, 2000  (DE)     100 60 030.1  
      Aug 25, 2001  (DE)     101 41 676.8--

Signed and Sealed this

Fifteenth Day of April, 2008

JON W. DUDAS  
*Director of the United States Patent and Trademark Office*